United States Patent [19]

Eriksson et al.

[11] Patent Number: 4,771,041

[45] Date of Patent: * Sep. 13, 1988

[54] METHOD FOR COMBATING VIRUS INFECTION

[75] Inventors: Bertil F. H. Eriksson, Tumba; Åke J. E. Helgstrand, Lund; Alfons Misiorny, deceased, late of Bandhagen; Karl H. Misiorny, legal representative, Södertälje; Göran B. Stening, Södertälje; Stig-Åke A. Stridh, Södertälje, all of Sweden

[73] Assignee: Astra Lakemedel Aktiebolag, Sweden

[*] Notice: The portion of the term of this patent subsequent to Jul. 29, 1997 has been disclaimed.

[21] Appl. No.: 793,575

[22] Filed: Oct. 31, 1985

Related U.S. Application Data

[60] Continuation-in-part of Ser. No. 589,164, Mar. 13, 1984, which is a division of Ser. No. 404,295, Aug. 2, 1982, which is a continuation of Ser. No. 179,038, Aug. 18, 1980, abandoned, which is a division of Ser. No. 971,931, Dec. 21, 1978, Pat. No. 4,339,445, which is a continuation-in-part of Ser. No. 807,783, Jun. 20, 1977, Pat. No. 4,215,113.

[30] Foreign Application Priority Data

Jul. 1, 1976 [SE] Sweden .................................. 7607496

[51] Int. Cl.$^4$ ............................................. A61K 31/66
[52] U.S. Cl. ....................................................... 514/120
[58] Field of Search ............................................ 514/120

[56] References Cited

U.S. PATENT DOCUMENTS 3,767,795 10/1973 Schleicher et al. .................. 514/120
3,836,650 9/1974 Schleicher et al. .................. 514/120

FOREIGN PATENT DOCUMENTS 492534  1/1976 Australia ............................. 514/120
2360797 6/1975 Fed. Rep. of Germany ...... 514/120
2126442 10/1972 France ............................... 514/120

OTHER PUBLICATIONS

Beilstein E 113, p. 103, (1942).
Beilstein E 111e, p. 240, (1961).
Chemical Abstracts, 83:73487n, (1975).
Nagvi et al., J. Chem. Soc. (A), 2751-2754, (1971).
Warren et al., J. Chem. Soc. (B), 618-621, (1971).
"Soon a Drug Against Aids will be Available", Arbet, Nov. 2, 1984, (including translation).
Oxford et al., "Conquest of Viral Diseases", May 1, 1985, Elsevier Science Publishers B.V., p. 591.
Sandstrom et al., "Inhibition of Human T-Cell Lymphotropic Virus Type III in Vitro by Phosphonoformate", The Lancet, Jun. 29, 1985, pp. 1480-1482.
Seligmann et al., "Aids—An Immunologic Reevaluation", The New England Journal of Medicine, vol. 311, No. 20, Nov. 15, 1984, pp. 1286-1291.
Montagnier et al., "Lymphadenopathy Associated Virus and AIDS", Clinical Immunology Newsletter, vol. 6, No. 5, May, 1985, pp. 65-68.

Primary Examiner—Jerome D. Goldberg
Attorney, Agent, or Firm—Brumbaugh, Graves, Donohue & Raymond

[57] ABSTRACT

A method for the selective treatment of virus infections in animals and man comprising administering to a host so infected a therapeutically effective amount of phosphonoformic acid or a physiologically acceptable salt thereof.

8 Claims, 4 Drawing Sheets

METHOD FOR COMBATING VIRUS INFECTION

This application is a continuation-in-part application of application Ser. No. 589,164, filed Mar. 13, 1984 which is a divisional application of application Ser. No. 404,295, filed Aug. 2, 1982 which is a continuation application of application Ser. No. 179,038, filed Aug. 18, 1980, now abandoned, which was a divisional application of application Ser. No. 971,931, filed Dec. 21, 1978, now U.S. Pat. No. 4,339,445, which is a continuation-in-part application of application Ser. No. 807,783, filed June 20, 1977, now U.S. Pat. No. 4,215,113.

FIELD OF THE INVENTION

The present invention relates to novel pharmaceutical compositions and to a novel method for selectively combating viruses, such as herpes viruses, influenza viruses, RNA tumor viruses, etc., which can cause various infectious diseases in animals including man.

BACKGROUND OF THE INVENTION

The effects of viruses on bodily functions is the end result of changes occuring at the cellular and subcellular levels. The pathogenic changes at the cellular level are different for different combinations of viruses and host cells. While some viruses use a general destruction (killing) of certain cells, other may transform cells to a neoplastic state.

Important common viral infections are herpes dermatitis (including herpes labialis), herpes keratitis, herpes genitalis, herpes zoster, herpes encephalitis, infectious mononucleosis and cytomegalovirus infections all of which are caused by viruses belonging to the herpesvirus group. Other important viral diseases are influenza A and B which are caused by influenza A and B virus respectively. Another important common viral disease is viral herpatitis and especially hepatitis B virus infections are widely spread. Effective and selective antiviral agents are needed for the treatment of these diseases.

A most important common feature of the interaction between viruses and cells is the replication of transcription of the specific viral genetic information carried by viral nucleic acids. These viral nucleic acids are of two kinds, deoxyribonucleic acids (DNA) or ribonucleic acids (RNA). The primary genetic information of the cell is carried by cell DNA. DNA and RNA synthesis involves complex enzymes called DNA and RNA polymerases respectively. The genetic information is transferred to nucleic acid transcripts and/or copies from a template nucleic acid. There are four general ways in which these nucleic acids can be replicated or transcribed 1. DNA (template) $\xrightarrow{\text{DNA-dependent}}$ DNA
   $\text{DNA polymerase}$ 2. RNA (template) $\xrightarrow{\text{RNA-dependent}}$ RNA
   $\text{RNA polymerase}$ 3. DNA (template) $\xrightarrow{\text{DNA-dependent}}$ RNA
   $\text{RNA polymerase}$ 4. RNA (template) $\xrightarrow{\text{RNA-dependent}}$ DNA
   $\text{DNA polymerase}$ (reverse transcriptase)

Processes 1 and 3 are used by cells. DNA viruses such as herpesviruses also use process 1 but the enzyme is different from that of the cell. RNA viruses such as influenza virus use process 2 and the RNA tumor viruses (retroviruses) can transcribe its RNA to DNA according to process 4.

The viral polymerases and the viral nucleic acid syntheses are essential for virus infections. DNA produced by DNA viruses such as herpesvirus or transcribed from RNA of RNA retroviruses and which carries the genetic information for cell transformation can be integrated into the host cell DNA. This integration, or later reactions as a consequence of integration (such a interaction with cancerogenic chemicals), can then lead to the transformation of the host cell. The implications of inhibiting reverse transcriptase for cell transformation are also described in U.S. Pat. No. 3,979,511.

Since the viral polymerases in most cases differ from the cellular ones these viral enzymes and viral nucleic acid syntheses are good targets for specific antiviral chemotherapy. There is a need for an effective antiviral agent preferably having a selective inhibiting effect on a specific viral function of the virus to be combated. It is, therefore, a general object of the present invention to provide a novel method for combating virus infections using an antiviral agent which exerts a selective inhibiting effect on viral functions but which exerts only a negligible inhibiting effect on functions of the host cells.

One especially undesired effect with available chemotherapeutic antiviral agents is that they may interact not only with the virus but also with components in the host cell.

The Invention

The invention provides a compound, and physiologically acceptable salts thereof, which compounds are useful in therapeutic and/or prophylactic treatment of viral diseases.

An effective selective antiviral agent with acceptable side effects should have a selective inhibiting effect on a specific viral function of the virus to be combated. It is, therefore, one object of the present invention to provide a novel method for combating virus infections using an antiviral agent which exerts a selective inhibiting effect on viral functions but which exerts only a negligible inhibiting effect on functions of the host cells.

The invention also relates to novel pharmaceutical compositions containing the antiviral agent.

Although the present invention relates broadly to a novel method for selectivity combating virus infections in animals and man, and pharmaceutical preparations to be used at such treatment, it will be particularly useful in the treatment of herpes virus infections, influenza virus infections, hepatitis B virus infections and retrovirus infections.

There are two major varities of influenza, commonly designated influenza A and influenza B. Another variety of influenza, designated influenza C also exists, but is not as frequently occuring as influenza A and B. These types of influenza are caused by virus commonly denoted influenza virus type A, B, and C, respectively.

An especially important area of use for the compositions of the present invention is in the treatment of herpes virus infections. Among the herpes viruses may be mentioned *Herpes simplex* type 1 and 2, varicella (*Herpes zoster*), virus causing infectious mononucleosis (i.e. Epstein-Barr virus) and cytomegalovirus. Important diseases caused by herpes viruses are herpes dermatitis, (including herpes labialis), herpes genitalis, herpes keratitis, herpes encephalitis and herpes zoster.

Other areas of use for the compositions of the present invention are in the treatment of infections caused by viruses such as papillomaviruses (i.e. warts), adenoviruses, poxviruses, hepatitis virus A and hepatitis virus B. Other possible areas of use for the compositions of the present invention are in the treatment of infections caused by picornaviruses, arboviruses, leucoviruses, arenaviruses, coronaviruses, rhabdoviruses, and paramyxoviruses, and for inhibiting the growth of virus transformed cells in animals and man. A particular area of use for the compositions of the present invention is in the inhibition of reverse transcriptases of RNA tumor viruses. The viruses in this group include all of the transforming sarcoma C-type viruses, the leucemia C-type viruses and the mammary B-type viruses.

It has been found according to the present invention that phosphonoformic acid of the structural formula

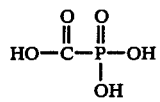

and physiologically acceptable salts thereof inhibits certain viral functions including tumorogenic functions and the multiplication of viruses. It selectively inhibits certain viral functions which are essential for the replication of the virus.

It has been found that phosphonoformic acid selectively inhibits a specific function of influenza virus, namely the influenza virion-associated RNA polymerase, while it does not affect either of the corresponding host cell polymerases, that is calf thymus DNA dependent RNA polymerase A and B. The said polymerases are enzymes which catalyze the synthesis of RNA in the host cell. It has also been found that phosphonoformic acid inhibits a specific function of herpes virus, namely the induced herpes simplex type 1 DNA polymerase. It is not active on *E. coli* DNA dependent RNA polymerase and *Micrococcus lysodeicticus* DNA dependent DNA polymerase. Inhibition of the viral polymerases means that the virus cannot replicate and thus the viral infection is prevented.

The invention furthermore provides:

A. A method for the treatment of diseases caused by viruses in animals including man, comprising administering to an animal so infected a therapeutically effective amount of a compound of the formula I or a physiologically acceptable salt thereof.

B. A method for the treatment of diseases caused by viruses in animals including man, by inhibiting the activity of viral polymerase, characterized by administering to an animal so infected a compound of the formula I or a physiologically acceptable salt thereof in an amount effective for inhibiting the activity of said viral polymerase.

C. A method for inhibiting the activity of reverse transcriptases of viruses in animals including man, by administration to an animal a compound of the formula I or a physiologically acceptable salt thereof in an mount sufficient for inhibiting the activity of said reverse transcriptase. Particular reverse transcriptases are the reverse transcriptases of retroviruses, such as visna, sarcoma and leucemia viruses. Further examples of retroviruses are given in section J (a).

D. A method for inhibiting the multiplication of virus, in particular herpes viruses, influenza virus and hepatitis B virus, and retroviruses in animals including man, by administering to an animal in need of such treatment a compound of the formula I or a physiologically acceptable salt thereof in an amount sufficient for inhibiting said multiplication.

E. A method for the treatment of virus-induced neoplastic diseases in animals including man, by inhibiting the multiplication of tumor viruses, characterized by administering to an animal in need of such treatment a compound of the formula I or a physiologically acceptable salt thereof in an amount sufficient for inhibiting such multiplication.

F. A method for the treatment of virusinduced neoplastic diseases in animals including man by inhibiting the activity or reverse transcriptase, characterized by administering to an animal so infected a compound of the formula I or a physiologically acceptable salt thereof in an amount effective for inhibiting the activity of said reverse transcriptase.

G. A method for the treatment of neoplastic diseases in animals including man, characterized by administering to an animal a therapeutically effective amount of phosphonoformic acid or a physiologically acceptable salt thereof.

The invention also relates to the use of a compound of the formula I or a physiologically acceptable salt thereof, in each of the above given methods A, B, C and D. For example, the invention relates to the use of a compound of the formula I or a physiologically acceptable salt thereof, for (a) inhibiting the replication of virus in animals including man, in particular herpes virus, influenza virus and hepatitis B viruses; and (b) for inhibiting the growth of virus-transformed cells in animals including man.

The compounds of the formula I and physiologically acceptable salts thereof are useful in therapeutic and/or prophylactic treatment of viral diseases and may be useful in therapeutic and/or prophylactic treatment of cancer caused by viruses.

The phosphonoformic acid may be formulated for use in human and veterinary medicine for therapeutic and prophylactic use. The compounds may be used in the form of a physiologically acceptable salt. Suitable salts are, e.g. amine salts, e.g. dimethylamine and triethylamine salt, ammonium salt, tetrabutylammonium salt, cyclohexylamine salt, dicyclohexylamine salt; and metal salts, e.g. mono-, di- and tri-sodium salt, mono-, di- and tripotassium salt, magnesium salt, calcium salt and zinc salt.

In clinical practice the phosphonoformic acid will normally be administered topically, orally, intranasally, by injection or by inhalation in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule, and such preparations comprise a further aspect of the invention. The compound may also be used without carrier material. As examples of pharmaceutical preparations may be mentioned tablets, drops such as nasal drops, eye drops, preparations for topical application such as ointments, jellies, creams and suspensions, aerosols for inhalation, nasal spray, liposomes, etc. Usually the active substance will comprise between 0.05 and 99, or between 0.1 and 99% by weight of the preparation, for example between 0.5 and 20% for preparations intended for injection and between 0.1 and 50% for preparations intended for oral administration.

In addition, the present invention may be practiced by the treatment of virus infections and diseases caused by viruses in animals and man (host) by a method in which a compound is administered to a host so inflicted which is converted to phosphonoformic acid or physiologically acceptable salts thereof in the body of said host in an amount effective to inhibit either replication of a virus.

To produce pharmaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax ® or other polyethylene glycol waxes and compressed to form tablets or cores for dragées. If dragées are required, the cores may be coated for example with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the preparation of soft gelatine capsules consisting of gelatine and, for example, glycerol and a plasticizer, or similar closed capsules, the active substance may be admixed with a Carbowax ® or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearate or stearic acid as lubricants.

By using several layers of the active drug, separated by slowly dissolving coatings sustained release tablets are obtained. Another way of preparing sustained release tablets is to divide the dose of the active drug into granules with coatings of different thicknesses and compress the granules into tablets together with the carrier substance. The active substance can also be incorporated in slowly dissolving tablets made for instance of fat and wax substances or evenly distributed in a tablet of an insoluble substance such as a physiologically inert plastic substance.

In order to obtain dosage units of the preparations—tablets, capsules etc.—which are designed so as to prevent release of and possible decomposition of the active substance in the gastric juice, the tablets, dragés etc. may be enteric-coated, that is provided with a layer of a gastric juice-resistant enteric film or coating having such properties that it is not dissolved at the acidic pH in the gastric juice. Thus, the active substance will not be released until the preparation reaches the intestines. As examples of such known enteric coatings may be mentioned cellulose acetate phtalate, hydroxypropylmethylcellulose phtalates such as those sold under the trade names HP 55 and HP 50, and Eudragit ®L and Eudragit ®S.

Effervescent powders are prepared by mixing the active ingredient with non-toxic carbonates or hydrogen carbonates of e.g. sodium, potassium or calcium, such as calcium carbonate, potassium carbonate and potassium hydrogen carbonate, solid, non-toxic acids such as tartaric acid, ascorbid acid, and citric acid, and for example aroma.

Liquid preparations for oral application may be in the form of elixirs, syrups or suspensions, for example solutions containing from about 0.1% to 20% by weight of active substance, sugar and a mixture or ethanol, water, glycerol, propylene glycol and optionally aroma, saccharine and/or carboxymethylcellulose as a dispersing agent.

For parenteral application by injection preparations may comprise an aqueous solution of a water soluble pharmaceutically acceptable salt of the active acids according to the invention, desirably in a concentration of 0.5–10%, and optionally also a stabilizing agent and/or buffer substances in aqueous solution. Dosage units of the solution may advantageously be enclosed in ampoules.

For topical application, especially for the treatment of herpes virus infections on skin, genitals and in mouth and eyes the preparations are suitably in the form of a solution, ointment, gel, suspension, cream or the like. The amount of active substance may vary, for example between 0.05–20% by weight of the active substance. Such preparations for topical application may be prepared in known manner by mixing the active substance with known carrier materials such as isopropanol, glycerol, paraffin, stearyl alcohol, polyethylene glycol, etc. The pharmaceutically acceptable carrier may also include a known chemical absorption promoter. Examples of absorption promoters are e.g. dimethylene acetamide (U.S. Pat. No. 3,472,931), trichloroethanol or trifluoroethanol) (U.S. Pat. No. 3,891,757), certain alcohols and mixtures thereof (British Pat. No. 1,001,949). A carrier material for topical application to unbroken skin is also described in the British patent specification No. 1.464.975 which discloses a carrier material consisting of a solvent comprising 40–70% (v/v) isopropanol and 0–60% (v/v) glycerol, the balance, if any, being an inert constituent of a diluent not exceeding 40% of the total volume of solvent.

The dosage at which the active ingredients are administered may vary within a wide range and will depend on various factors such as for example the severity of the invention, the age of the patient, etc., and may have to be individually adjusted. As a possible range for the amount of phosphonoformic acid which may be administered per day may be mentioned from about 0.1 mg to about 2000 mg or from about 1 mg to about 2000 mg, or preferably from 1 mg to about 2000 mg for topical administration, from 50 mg to about 2000 mg or from 100 to about 1000 mg for oral administration and from 10 mg to about 2000 mg or from 50 to about 500 mg for injection. In severe cases it may be necessary to increase these doses 5-fold to 18-fold. In less severe cases it may be sufficient to use up to 500 or 1000 mg.

The pharmaceutical compositions containing the active ingredients may suitably be formulated so that they provide doses within these ranges either as single dosage units or as multiple dosage units.

Thus, it has been found according to the invention that phosphonoformic acid, and the physiologically acceptable salts thereof can be used to selectively inhibit viral functions of herpes virus and influenza virus. Since the functions in question are essential for the replication of the virus, phosphonoformic acid and physiologically acceptable salts thereof are useful in therapeutic and/or prophylactic treatment of virus infections.

A preferred aspect of the invention is the use of phosphonoformic acid or a physiologically acceptable salt thereof, in the treatment of herpes virus infections.

Phosphonoformic acid is a known compound. Its synthesis and its trisodium salt are described e.g. by Nylén, Chem. Berichte 578: 1023–1038 (1924). Since phosphonoformic acid is unstable in its free acid form, it is preferably used in the form of its salts.

BIOLOGICAL TESTS

The inhibiting effect of phosphonoformic acid on influenza and herpes virus was tested using the methods described below. The test method for testing of the effect of phosphonoformic accid on host cell functions are also described below. In the experiments A-K phosphonoformic acid was used in the form of its trisodium salt.

I. Inhibition of viral and cellular polymerases

Polymerases, nucleic acid template nucleoside triphosphates, of which guanosine triphosphate is tritium-labelled, salt and buffer are mixed at 0° C. in a total volume of 125 µl (for herpes DNA polymerase, see F. below). The concentrations of the nucleoside triphosphates UTP (uridine triphosphate), CTP (cytidinetriphosphate), GTP (guanosinetriphosphate) and ATP (adenosinetriphosphate) were generall 400, 400, 400, and 2000 µM, respectively. The test compound is also added in various concentrations to the mixture obtained. A standard mixture without test compound is also prepared using the same amounts of the ingredients. The enzyme reaction, i.e. synthesis of nucleic acid, is started by incubating the mixture at 37° C. For influenza RNA polymerases the temperature is 33° C. The reaction is allowed to proceed for 60 minutes in the assay of influenza and Micrococcus polymerases. For E.coli DNA dependent RNA polymerase the time is 20 min. and for herpes DNA polymerase 30 minutes. The incubation time for calf thymus polymerases is 10 minutes. The incorporation of labelled monomer into trichloroacetic acid insoluble nucleic acid product was measured in the following way. Before and after the incubation period 50 µl are withdrawn from the mixture and applied to filter discs. These are put in 5% trichloroacetic acid solution and washed several times. After drying the discs are measured for radioactivity in a liquid scintillation counter. The difference in radioactivity between samples with and without added compound is used to calculate the inhibition of the polymerase activity. The inhibition is expressed as percentage inhibition using the radioactivity of the standard sample as basis.

A. Inhibition by phosphonoformic acid of type A influenza virion associated RNA polymerase Influenza $A_2$ Aichi virus was purified according to the method of Pons and Hirst, Virology 34 385 (1968). The assay mixture is described by Bishop, Obijeski and Simpson, J. Virol. 8 66 (1971). The inhibitory effect of phosphonoformic acid is shown in Table 1 below.

TABLE 1

| Inhibition by phosphonoformic acid of type A influenza virion-associated RNA polymerase | |
|---|---|
| Conc. of phosphonoformic acid (µM) | Inhibition[a] (%) |
| 0.1 | 21 |

TABLE 1-continued

| Inhibition by phosphonoformic acid of type A influenza virion-associated RNA polymerase | |
|---|---|
| Conc. of phosphonoformic acid (µM) | Inhibition[a] (%) |
| 0.50 | 67 |
| 1.00 | 79 |
| 10 | 91 |
| 100 | 95 |
| 500 | 93 |

[a]mean of two experiments

In a modified version of the test, carried out essentially as described by Pons and Hirst (loc. cit) but modified so that the assay mixture did not contain $Mn^{2+}$ ions, it was found that phosphonoformic acid in a concentration of 20 µM gave 50% inhibition of the polymerase activity.

B. Inhibition by phosphonoformic acid of type B influenza virion associated RNA polymerase Polymerase from influenza B Hongkong 8/73 was assayed in the same way as for influenza $A_2$ Aichi in experiment A. The inhibitory effect of phosphonoformic acid is shown in Table 2 below.

TABLE 2

| Inhibition by phosphonoformic acid of Type B influenza virion-associated RNA polymerase[a] | |
|---|---|
| Conc. of phosphonoformic acid (µM) | Inhibition (%) |
| 1.0 | 77 |
| 500 | 100 |

[a]In this experiment the concentration of GTP was 135 µM.

C. Inhibition by phosphonoformic acid of calf thymus DNA dependent RNA polymerase Purification of the enzymes was carried out according to the method of Kedinger et al, Eur. J. Biochem. 28 269 (1972). The enzyme fractions DCB and DCA were used for all experiments. The assay mixture of Kedinger, loc.cit., was used. The test results are given in Table 3 below.

TABLE 3

| Inhibition by phosphonoformic acid of calf thymus DNA dependent RNA polymerase fraction B and A | | |
|---|---|---|
| Conc. of phosphonoformic acid (µM) | Inhibition % | |
|  | DCB | DCA |
| 500 | 0 | −3 |

D. Inhibition by phosphonoformic acid of E. coli DNA dependent RNA polymerase

The enzyme was bought from Sigma. The template used was DNA extracted from E. coli according to Marmur, J. Mol. Biol. 3 208 (1961) and the assay mixture essentially that described by Burgess, J. Biol. Chem. 244 6160 (1969). The test results are given in Table 4.

TABLE 4

| Inhibition by phosphonoformic acid of E. coli dependent RNA polymerase | |
|---|---|
| Conc. of phosphonoformic acid (µM) | Inhibition (%) |
| 500 | 3 |

E. Inhibition by phosphonoformic acid of Micrococcus luteus DNA dependent DNA polymerase The polymerase was bought from Sigma and assayed essentially according to Harwood et al., J. Biol. Chem. 245: 5614 (1970).

The test results are given in Table 5 below.

TABLE 5

Inhibition by phosphonoformic acid of *Micrococcus luteus* DNA dependent DNA polymerase

| Conc. of phosphonoformic acid (μM) | Inhibition (%) |
|---|---|
| 500 | 6 |

F. Inhibition by phosphonoformic acid of herpes simplex virus type 1 induced DNA polymerase.

Purification of the enzyme was carried out according to the method of Weissbach et al., J. Biol. Chem. 248 6270 (1973).

The assay mixture (200 μl) contained 200 μg/ml activated calf thymus DNA and 0.05 mM [3H] dTTP (specific activity 130 cpm per pmole).

All other ingredients were according to Weissbach (see above).

The results are given in table 6.

TABLE 6

Inhibition by phosphonoformic acid of herpes simplex virus type 1 induced DNA polymerase

| Conc. of phosphonoformic acid (μM) | Inhibition (%) |
|---|---|
| 5 | 15 |
| 20 | 43 |
| 100 | 76 |
| 500 | 90 |

II. Inhibition of virus multiplication in cell cultures

The inhibition of influenza virus and herpes virus by phosphonoformic acid has been measured as plaque reaction according to the following procedures.

G. Inhibition by phosphonoformic acid of influenza (WSN Wilson Smith Neurotropic type A.) plaque The method for plaque assay of influenza has been described by Bentley et al., Archiv fur die Gesamte Virusforschung 33 (1971) 234. Monolayers of MDCK (Madin Darby Canine Kidney) cells on 5 cm plastic petri dishes were inoculated with 100 plaque-forming units of influenza virus (WSN). After virus adsorption, 5 ml of agarose overlay containing different concentrations of phosphonoformic acid was added and the plates were incubated at 34° C. for 4 days. The plaques formed at this time were counted. The results are shown in Table 7.

TABLE 7

Inhibition by phosphonoformic acid of influenza virus (WSN) plaque on MDCK monolayers.

| Conc. of phosphonoformic acid (μM) | Inhibition[a] (%) |
|---|---|
| 100 | 10 |
| 250 | 50 |
| 500 | 95 |

[a] a mean of three different experiments

H. Inhibition by phosphonoformic acid of herpes simplex type 1 plaque

The plaque reduction assay for herpes simplex type 1 was performed on GMK (Green Monkey Kidney) cells as described by Ejereito et el., J. Gen. Virol. 2 (1968) 357. Monolayers on 5 cm petri dishes were used and after virus adsorption phosphonoformic acid was added in the medium. The results are shown in table 8.

TABLE 8

Inhibition by phosphonoformic acid of herpes simplex type 1 plaque on GMK monolayers.

| Conc. of phosphonoformic acid (μM) | Inhibition[a] (%) |
|---|---|
| 1 | 0 |
| 15 | 50 |
| 100 | 90 |

[a] mean of three different experiments

I. Inhibition by phosphonoformic acid of herpes simplex type 2 plaque

The plaque reduction assay for herpes simplex type 2 was performed in the same way as in experiment H. The results are shown in Table 9.

TABLE 9

Inhibition by phosphonoformic acid of herpes simplex type 2 patient isolates plaque on SIRC (Staatens-Seruminstitut Rabbit Cornea) monolayers

| Conc. of phosphonoformic acid (μM) | Inhibition (%) |
|---|---|
| 500 | 99.9 |

J. The utility of phosphonoformic acid in the treatment of retroviruses, as outlined previously, is supported by the following tests, where it is shown (a) that phosphonoformic acid inhibits reverse transcriptase of retroviruses.

(b) that phosphonoformic acid inhibits visna virus (a retrovirus) growth.

(a) INHIBITION OF REVERSE TRANSCRIPTASE BY PHOSPHONOFORMIC ACID

Phosphonoformic acid has been found to inhibit reverse transcriptase which is an enzyme common to all retroviruses.

Methods

Reverse transcriptase from various retroviruses have been tested in cell-free assays for inhibition by phosphonoformic acid and phosphonoacetic acid. The assay conditions have been described by Collaborative Research, Inc, 1365 Main Street, Waltham, Mass., USA "Assay kit for mammalian viral reverse transcriptase". BLV and VV were prepared in this laboratory and all other viruses and viral enzyme were obtained from Dr. K Nilsson, Department of Pathology, University of Uppsala and from Boehringer Mannheim, Germany. Phosphonoformic acid (PFA) and phosphonoacetic acid (PAA) were added at pH 7.2 to the reaction mixtures at the start of the reaction.

Abbreviations

Rauscher murine leukemia virus; RMuLV, visna virus; VV, avian myeloblastosis virus; AMV, bovine leukemia virus; BLV, baboon endogenous virus; BaEV, simian sarcoma virus; SSV.

Results

The comparison of the inhibition by phosphonoformate and phosphonoacetate of the various enzymes is shown in table 10.

Conclusion

It is seen in Table 10 that phosphonoformic acid inhibits reverse transcriptase from several retroviruses at concentrations where phosphonoacetic acid is not inhibitory.

TABLE 10

Inhibition of various reverse transcriptase activities by PFA and PAA

| Enzyme source | Template/ primer | μM PFA 10 | μM PFA 100 | μM PFA 500 | μM PAA 10 | μM PAA 100 | μM PAA 500 |
|---|---|---|---|---|---|---|---|
| RMuLV | $(rA)_n \cdot (dT)_{10}$ | 90 | 96 | >99 | 0 | 10 | 35 |
| VV | $(rA)_n \cdot (dT)_{10}$ | ND | 95 | 99 | ND | 25 | 3 |
| BLV | $(rA)_n \cdot (dT)_{10}$ | ND | 88 | 93 | ND | 0 | 10 |
| BaEV | $(rA)_n \cdot (dT)_{10}$ | 96 | >99 | >99 | 5 | 58 | 71 |
| SSV | $(rA)_n \cdot (dT)_{10}$ | 92 | >99 | >99 | 0 | 44 | 58 |
| AMV | $(rA)_n \cdot (dT)_{10}$ | 43 | 94 | 99 | 0 | −34 | −86 |
| AMV | endogenous | 15 | 49 | 70 | 0 | −2 | −3 |
| AMV, purified enzyme | $(rA)_n \cdot (dT)_{10}$ | 45 | 96 | >99 | 0 | 0 | 19 |

ND: not detectable

(b) INHIBITION BY PHOSPHONOFORMIC ACID OF VISNA VIRUS GROWTH IN SHEEP CHORIOPLEXUS CELLS

Visna virus is a retrovirus that can multiply in sheep choroid (SCP) cells. The infection can be followed by titrating medium from infected cells to determine the formation of virus particles and by observing morphological changes as syncytial formation and cell degeneration.

Methods

Plates (5 cm) with primary SCP cells in medium 199 with 10% sheep serum were grown to confluence and then infected with $1 \times 10^6$ TCID$_{50}$ (tissue culture infectious doses) of visna virus. One set of plates were left untreated, one set received different concentrations of phosphonoformic acid (PFA) at pH 7.2. Another set received phosphonoacetic acid (PAA) at pH 7.2. Uninfected plates were used as controls with and without PFA and PAA. The virus titre was determined 5 days after infection by the end-point titration method. The plates were checked daily in a light microscope to observe morphological changes.

Results

FIG. 1 shows the effect of increasing concentrations of PFA and PAA on the growth of visna virus in SCP cells. The morphological changes were observed at indicated days after infection as shown in table 11. The effect caused by PFA is reversible and cells degenerate after removal of PFA.

Conclusion

PFA, but not PAA, can prevent degeneration of visna virus infected cells. This prevention is reversible. A 50 percent reduction of virus multiplication is obtained at 20 μM PFA whereas 500 μM PAA does not prevent virus multiplication.

TABLE 11

| Cells | Treatment | Morphological changes Day 3 | Day 5 | Day 7 |
|---|---|---|---|---|
| Uninfected | None | − | − | − − |
| Visna virus infected | None | ++ | +++ | ++++ |
| Visna virus infected | 100 μM PFA | − | + | ++ |
| Visna virus infected | 500 μM PFA | − | − | + |
| Uninfected | 100 μM PFA | − | − | − |
| Uninfected | 500 μM PFA | − | − | − |
| Visna virus infected | 500 μM PAA | + | ++ | ++++ |
| Uninfected | 500 μM PAA | − | − | − |

− no change
+ 10% cell degeneration
++ 25% cell degeneration
+++ 75% cell degeneration
++++ 100% cell degeneration

(c) EFFECT OF PHOSPHONOFORMIC ACID ON THE SURVIVAL OF MICE BEARING YBA AND EHRLICH ASCITES TUMORS

The inhibition of reverse transcriptase by phosphonoformic acid (PFA) has prompted an investigation of the effect of PFA on animals with tumors where retroviruses are implicated. Ehrlich ascites tumors (Friend virus) in NMRI mice and YBA solid tumors (Moloney virus) in CBA mice have been used.

Methods

NMRI mice were inoculated intraperitoneally with 0.1 ml of a 1/10 dilution of ascitic fluid from a mouse with an Ehrlich ascites tumor. Nine mice were given intraperitoneally 100 mg/kg of PFA per day as a 2% solution at pH 7.2, and 9 mice were treated with 0.95% NaCl ip. CBA mice were inoculated with $7 \times 10^6$ cells subcutaneously in the flank. Fifteen CBA mice were given 0.5% PFA at pH 7.2 in the drinking water and fifteen water without addition.

Toxicity controls with substance were given to uninfected animals.

Results

Conclusions

Figure 1:
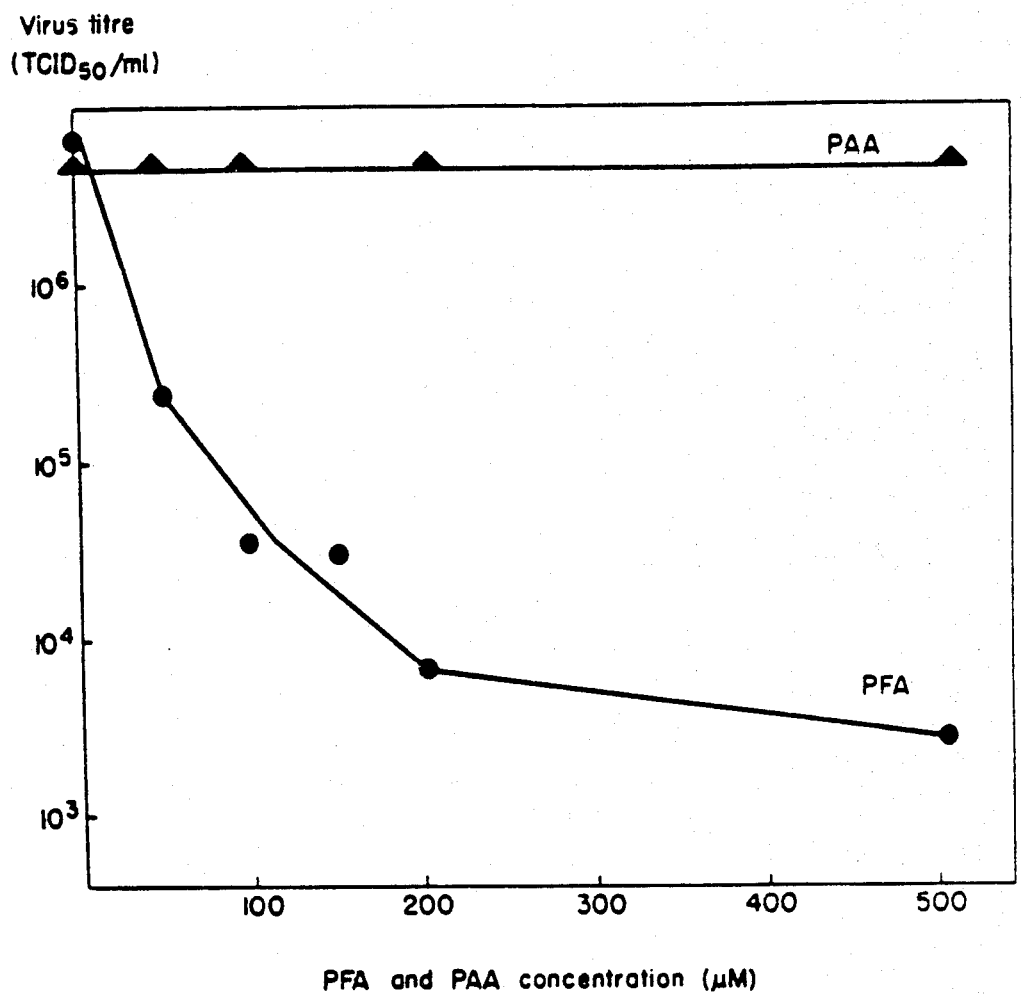
Figure 2:
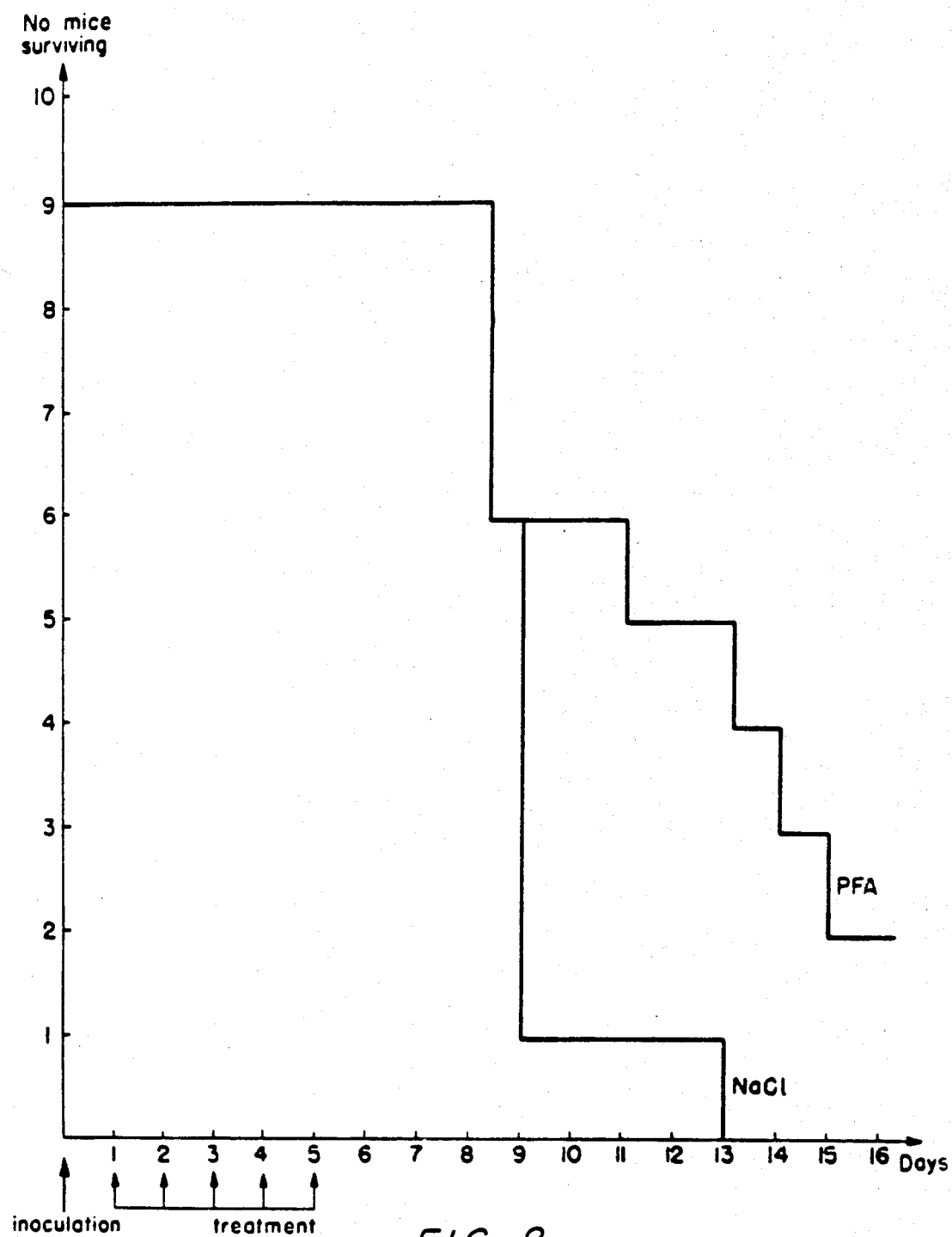
FIG. 2 shows the increased survival of mice inoculated with Ehrlich ascites cells after treatment with PFA ip when compared to the control where the mice received 0.95% NaCl instead of PFA. No mice died in the toxicity control group (10 animals) where uninfected mice were given 100 mg/kg/day PFA.
Figure 3:
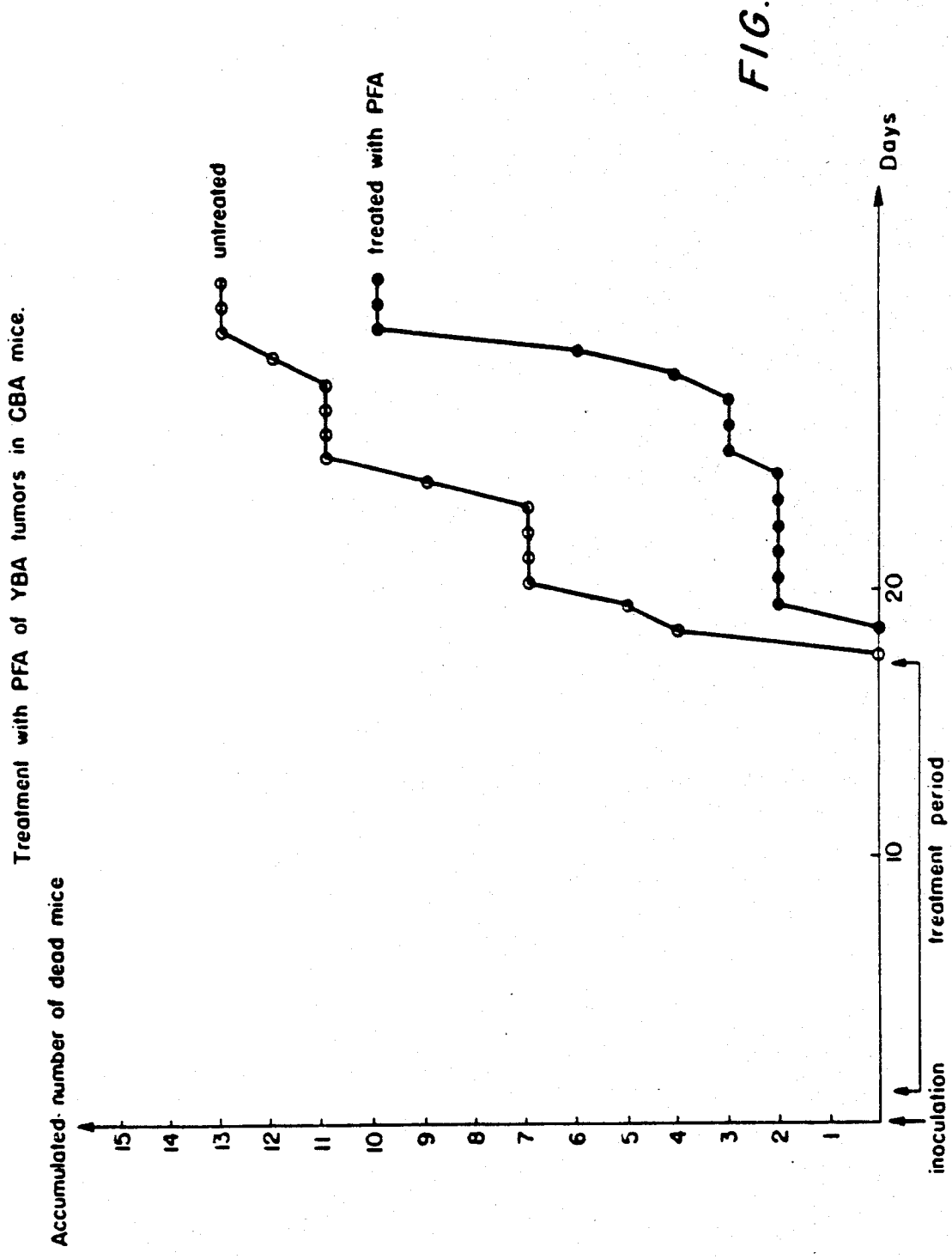
FIG. 3 shows the increased survival of mice inoculated with YBA cells after treatment with 0.5% PFA in the drinking water. No mice died in the substance control group (10 mice).

An increased survival was observed when mice with Ehrlich ascites and YBA tumors were treated with PFA.

J-I.

It has also been discovered by Dr. Bo Oberg that phosphonoformic acid used in accordance with the present invention inhibits the replication of HTLV-III/-LAV/ARV, the retroviruses associated with causation of the Acquired Immunodeficiency Syndrome (AIDS). The invention wherein phosphonoformic acid is used as a treatment is the subject of the companion application Ser. No. 793,576 of Oberg, "Method of Control and Treatment of Acquired Immunodeficiency Syndrome (AIDS)" filed herewith.

Materials and Methods

Source of HTLV-III Reverse Transcriptase and Assay Conditions

HTLV-III reverse transcriptase used in these studies was purified by sequential chromatography on DEAE cellulose, phosphocellulose and hydroxyapatite. The purified enzyme was stored in 50 mM Tris-HCl (pH 7.5), 1 mM dithiothreitol (DTT), 0.01% Triton X-100 and 20% glycerol. Reverse transcriptase assays were carried out in a reaction mixture (50 μl) containing 50 mM Tris-HCl (pH 7.5), 5 mM DTT, 100 mM potassium chloride, 0.01% Triton X-100 or NP40, 10 μg/ml $(dT)_{15} \cdot (A)_n$ as template primer and /$^3$H/-deoxythymidine triphosphate (/$^3$H/-dTTP). The reaction mixture was incubated for 1 hour at 37° and the reaction was stopped by the addition of 50 μg of yeast tRNA and 2 ml of 10% solution of trichloroacetic acid (TCA) containing 1 mM sodium pyrophosphate. The samples were filtered on millipore filters (0.45 μm), washed first with 5% TCA solution (5 times) and then with 2 ml of 70% ethanol. The filters were dried under a heat lamp, scintillation fluid was added and the radioactivity counted in a β-scintillation counter.

HTLV-III Infection of H9 Cells

H9 cells constitute a human cell line that can be chronically infected with HTLV-III virus. (Science 1984; 224: 497–500). H9 cells were treated with polybrene (2 μg/ml) for 30 min. at 37° C., washed free of polybrene and infected with $2 \times 10^8$ HTLV-III virus particles per $4 \times 10^5$ H9 cells. The positive control sample did not receive any drug whereas the test samples received various concentrations of foscarnet. The cultures were analyzed for HTLV-III reverse transcriptase activity as described above.

Results

The effect of foscarnet on purified HTLV-III reverse transcriptase (RT) was assayed as a function of drug concentration.

The concentration of foscarnet causing 50% inhibition of HTLV-III reverse transcriptase activity from different virus isolates was found to be between 0.1 μM and 2 μM. Similar results were obtained when the effect of foscarnet was studied on the endogenous reverse transcriptase activity of the disrupted virus in the absence of an exogenously added template-primer such as $(dT)_{15}.(A)_n$. The inhibition of reverse transcriptase by foscarnet has been shown to be noncompetitive with respect to substrate and uncompetitive with respect to template.

The effect of foscarnet on the replication of HTLV-III in H9 cells was determined as a function of both foscarnet concentration and time of incubation. The degree of inhibition is dependent on both the time of incubation and the foscarnet concentration and an inhibition of 50% was seen at 50 μM foscarnet after 6 days of incubation. A concentration of 300 μM was sufficient to obtain more than 95% inhibition after six days of incubation.

K. Acute Toxicity

Phosphonoformic acid was tested for acute toxicity in mice. The compound (as its sodium salt) was given as solution i.p. in doses of 250, 500, 1000, 2000 and 4000 μmol/kg. Groups of 4 male mice of NMRI strain weighing 18.5–20.5 g were used for each dose. LD50 was found to be between 4000 and 2000 μmole/kg body weight.

L. Other animal experiments

Preliminary experiments on cutaneous herpes type 1 infected guinea pigs have shown that phosphonoformic acid as its trisodium salt in topical preparations according to examples 15, 16 and 17 below has a therapeutic effect.

M. Test on skin irritating properties

The skin irritating properties of phosphonoformic acid in comparison with the skin irritating properties of the prior art compound phosphonoacetic acid was investigated.

1. Test on Guinea pigs

Test compounds

Phosphonoformic acid and phosphonoacetic acid were used as their trisodium and disodium salts, respectively. The test substances were used in 1% solutions.

Test method

Guinea-pigs of the Dunkin-Hartley strain of both sexes and weighing 200–300 g were used. The back of the animal was shaved and depilated with Opilca ® on the day before starting the application of the solutions. The back was divided into six squares in the middle of which 30 μl of the test solutions was applied. In a given group of animals the different solutions were applied in a randomized order alternating between sites. However, the same site was used for repeated application of a given solution.

The irritation was scored on scales of 0 to 3, each grade corresponding to the following specific criteria of irritation:

0=no irritation
1=slight erythema or edema or no hair growth
2=moderate erythema or edema or skin discoloration
3=marked erythema or edema or necrosis including crust formation.

The scoring was carried out blindly using coded solutions.

The scores of all the applications for a given solution and time were added and the average score was calculated.

The solvent used was a mixture of glycerol 10.0% (w/v), Tween 80 0.1% and aq sterile ad 100. All solutions were adjusted to pH 6.5 with hydrochloric acid or aqueous sodium hydroxide as required. Thirty μl of 1.0% solutions of phosphonoformic acid and phosphonoacetic acid respectively was applied twice daily during three days to each of six guinea pigs.

Test results

Figure 4:
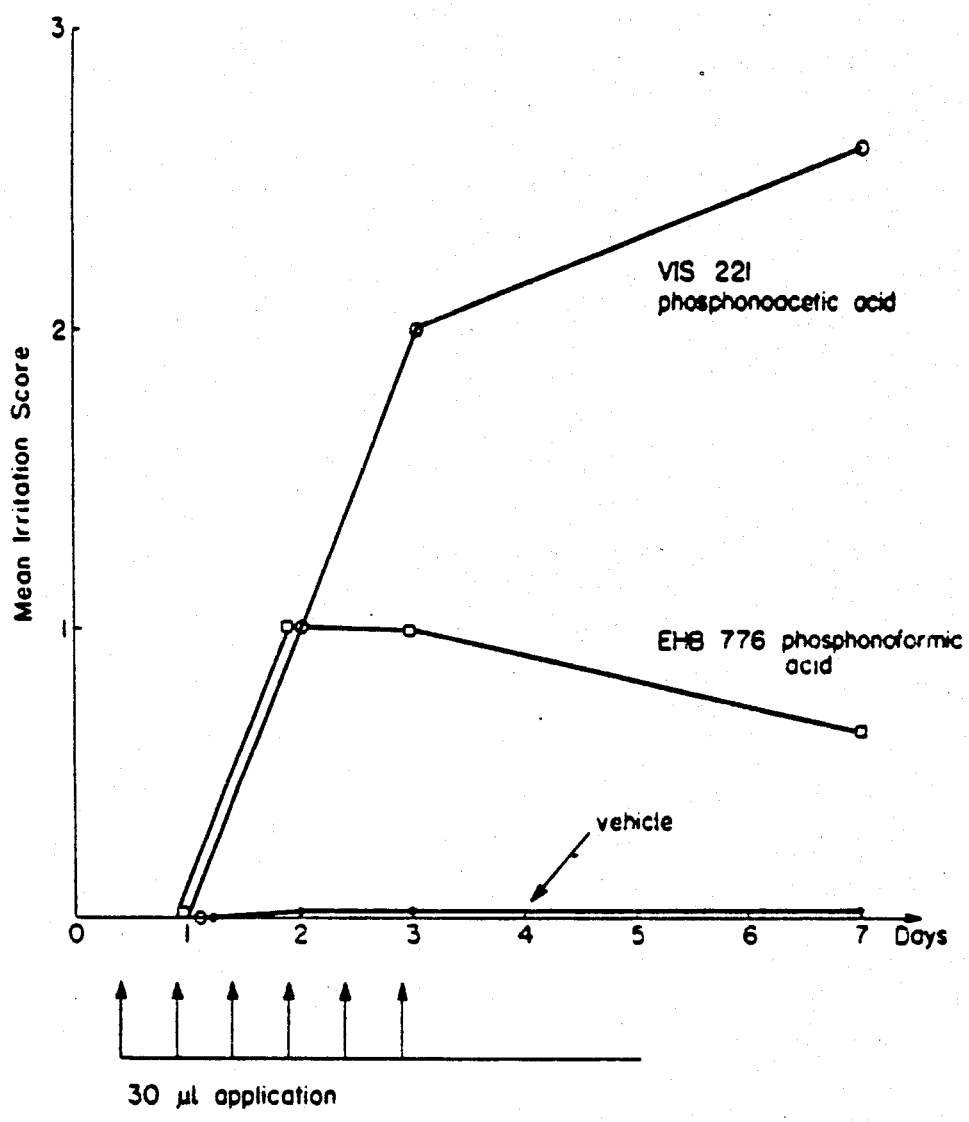

The test results are given graphically in FIG. 4. The solution of phosphonoacetic acid of the prior art gave rise to marked local irritation from day 4 and onwards (score 2–3). A pronounced erythema followed by crust formation was developed.

The irritating effect of the corresponding solution of phosphonoformic acid utilized in the invention was practically negligible (score <1). The degree of erythema on day 4 was only slight. The vehicle was not irritating.

A similar study of phosphonoacetic acid in which the animals were studied during 15 days showed that the skin heals after about two weeks but remains hairless. For phosphonoformic acid the skin is normal with hair after two weeks.

2. Test in Cynomolgus monkeys

Test compounds

Phosphonoformic acid, also denoted PFA and phosphonoacetic acid, also denoted PAA were used in the form of their trisodium and disodium salt, respectively. The following equimolar compositions of the two test compounds were used:

| 2% w/w PFA cream (CHB 776 cream, batch F7, 2% w/w) | |
|---|---|
| Trisodium phosphonoformate | 2.0 |
| Arlatone 983 | 4.0 |
| Cetanol | 2.0 |
| Stearic acid | 2.0 |
| Parafin oil | 2.0 |
| Propylene glycol | 2.0 |
| Glycerol | 1.5 |
| Metagin | 0.06 |
| Propagin | 0.03 |
| Dist. water ad | 100 |
| pH adjusted to | 8.0 |
| 1.78% w/w PAA cream (VIS 221 cream, batch F13, 1.78 (w/w) | |
| Disodium phosphonoacetate | 1.78 |
| Arlatone 983 | 4.0 |
| Cetanol | 2.0 |
| Stearic acid | 2.0 |
| Parafin oil | 2.0 |
| Propylene glycol | 2.0 |
| Glycerol | 1.5 |
| Metagin | 0.06 |
| Propagin | 0.03 |
| Dist. water ad | 100 |

| pH adjusted to | 8.0 |

Method

Two adult male Cynomolgus monkeys were treated once daily for 7 days with PFA or PAA in Arlatone cream. Treatment was done both by topical application of 0.2 ml cream on an area of 3×7 cm on the upper part of the arms and by application of 0.2 ml of cream on the penis and the adjacent skin. During application of cream, the animals were lightly anaesthetized with Ketalar®, given intramuscularly. All applications were 0.2 ml each on day 6/3, 7/3, 8/3, 9/3, 10/3, 11/3 and 12/3 1978.

Test results

The test results are given as in Table 12.

TABLE 12

Comparison of skin irritation caused by equimolar concentrations of phosphonoformic acid (PFA) and phosphonoacetic acid (PAA) in Cynomolgus monkeys

| Animal no. | Test compound | Area of application | Result |
| --- | --- | --- | --- |
| 38:77 | Phosphonoacetic acid | penis | Glans penis and adjacent skin areas irritated 9/3–12/3 Adjacent skin areas also showed symptoms 23/3 |
| | Phosphonoacetic acid | left upper arm | Severe skin irritation on day 12/3, remaining symptoms 23/3. |
| 35:77 | Phosphonoacetic acid | left upper arm | Skin irritation on day 12/3, remaining symptoms 23/3 |
| 38:77 | Phosphonoformic acid | right upper arm | No symptoms |
| 35:77 | Phosphonoformic acid | penis | No symptoms |
| 35:77 | Phosphonoformic acid | right upper arm | No symptoms |

Discussion of the test results

The purpose of tests A, B and G above is to ascertain the effect of the phosphonoformic acid against influenza viruses. The purpose of tests F, H and I is to ascertain the effect of phosphonoformic acid against herpes viruses. The purpose of tests C, D and E is to ascertain the absence of effect of phosphonoformic acid on cellular polymerases. The purpose of tests J a, b and c is to ascertain the effect of phosphonoformic acid on reverse transcriptase and or retrovirus. As seen in tables 1 and 2, respectively, phosphonoformic acid inhibits the influenza A virus polymerase activity to more than 50% at concentration of 0.5 $\mu$M and influenza B virus polymerase to more than 50% at a concentration of 1.0 $\mu$M. At test in assay solution free from $Mn^{2+}$ ions, phosphonoformic acid inhibited influenza A virus polymerase activity to 50% at a concentration of 20 $\mu$M. As seen in table 7, phosphonoformic acid inhibits the corresponding plaque formation to 50% at a concentration of 250 $\mu$M. As seen in tables 6, 8 and 9, respectively, phosphonoformic acid inhibits the herpes simplex virus type 1 induced DNA polymerase activity to more than 50% at a concentration of 100 $\mu$M, the plaque formation of herpes simplex virus type 1 to 50% at a concentration of 15 $\mu$M and plaque formation of the herpes virus type 2 to more than 99.9% at 500 $\mu$M. In tables 3, 4 and 5 it is seen that phosphonoformic acid has no significant effect against calf thymus DNA dependent RNA polymerases, or 0% and −3% inhibition respectively, at a concentration of 500 $\mu$M, that it is practically inactive against E. coli DNA dependent RNA polymerase, or 3% inhibition at a concentration of 500 $\mu$M, and that it is practically inactive against Micrococcus luteus DNA dependent DNA polymerase, or 6% inhibition at a concentration of 500 $\mu$M. The acute toxicity of phosphonoformic acid is low, i.e. $LD_{50}$ between 2000 and 4000 $\mu$mole/kg i.p. in mice. Thus, phosphonoformic acid exerts a selective effect on influenza and herpes viruses. The selective effect of phosphonoformic acid on the viral polymerases gives a molecular basis for a selective antiviral effect in animals including man.

It is seen in test J (a) that phosphonoformic acid inhibits reverse transcriptase from a number of viruses. In test J (b) it is seen that phosphonoformic acid inhibits the growth of a specific virus (visna virus) which virus utilizes reverse transcriptase for its multiplication. In test J (c) it is demonstrated that administration of phosphonoformic acid gives a prolonged survival time in experimental animals with tumors induced by retroviruses. Thus, the results of tests J a, b and c supports the utility of phosphonoformic acid in the uses A to I inclusive given previously in this specification.

In the tests M on dermal toxicity (skin irritating properties) of phosphonoformic acid of the present invention and phosphonoacetic acid of the prior art it is seen that phosphonoacetic acid is very irritating to the skin. The irritating effect of trisodium phosphonoformate was found to be practically negligible (score $\leq 1$) while phosphonoacetic acid gave rise to a marked local irritation (score 2–3). In the test on Cynomolgus monkeys (Table 12) these results are fully confirmed, namely that phosphonoacetic acid is a compound which exhibits a very high dermal toxicity.

The difference established between phosphonoformic acid and phosphonoacetic acid is a difference in kind and not a difference in degree.

The test results on the dermal toxicity of phosphonoacetic acid of the prior art indicate that phosphonoacetic acid is not suitable for clinical use against skin infections including infections caused by herpes virus.

Salts of phosphonoformic acid

Physiologically acceptable salts of phosphonoformic acid are prepared by methods known in the art as illustrated in the following. Metal salts can be prepared by reacting a metal hydroxide with an alkylester of phosphonoformic acid. Examples of metal salts of phosphonoformic acid which can be prepared in this way are salts containing Li, Na, K, Ca, Mg, Zn, Mn and Ba. A less soluble metal salt can be precipitated from a solution of a more soluble salt by addition of a suitable metal compound. Thus for examples, Zn, Mg and Mn salts of phosphonoformic acid can be prepared from phosphonoformic sodium salts. The metal ion of a metal salt of phosphonoformic acid can be exchanged by hydrogen ions, other metal ions, ammonium ion and ammonium ions substituted by one or more organic radicals by using a cation exchanger as shown in the following examples.

EXAMPLE 1

Disodium salt of phosphonoformic acid

Phosphonoformic acid trisodium salt (1.30 g) was dissolved in 50 ml of water. To this solution a cation exchanger Dowex 50 W×2 in acid form was added with stirring until a pH of 5.35 was obtained. The ion exchanger was filtered off and the filtrate evaporated at a reduced pressure. The residue was triturated with ethanol with cooling. The yield of disodium salt was 0.65 g. It contained 8.3% water. Titration as base gave equivalent weight 168.2 (corrected for 8.3% water) and Na 27.3% (corrected for water). Calculated for $CHO_5P.2Na$, formula weight 170.0, Na 27.1%.

EXAMPLE 2

Monocyclohexylammonium salt of phosphonoformic acid

A cation exchanger Dowex 50 W×2 (75 g) in acid form was saturated with cyclohexylamine (10 g), poured into a column (diameter 2 cm) and washed free from excess of cyclohexylamine. A water solution of phosphonoformic acid trisodium salt (1.3 g in 40 ml of water) was slowly passed through the column followed by about 100 ml of water and the combined eluate evaporated at a reduced pressure. The salt obtained was recrystallized from ethanol-water. The final product was crystalline and had a melting-point of 215°–218° C. (decomposition) and contained 27.0% of water. Titration as acid gave equivalent weight 220.5 (corrected for 27.0% water). Calculated for $CH_3O_5P.C_6H_{13}N$ formula weight 225.2. The NMR spectrum indicated that the salt contained only one cyclohexylamine residue (a minor impurity in form of ethanol was detected).

Examples of other useful salts which can be prepared in this way are the salts of the formula

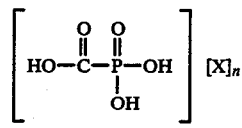
II in which formula n is 1, 2 or 3 and X is a salt-forming component such as $NH_3$, $CH_3NH_2$, $C_2H_5NH_2$, $C_3H_7NH_2$, $C_4H_9NH_2$, $C_5H_{11}NH_2$, $C_6H_{13}NH_2$, $(CH_3)_2NH$, $(C_2H_5)_2NH$, $(C_3H_7)_2NH$, $(C_4H_9)_2NH$, $(C_5H_{11})_2NH$, $(C_6H_{13})_2NH$, $(CH_3)_3N$, $(C_2H_5)_3N$, $(C_3H_7)_3N$, $(C_4H_9)_3N$, $(C_5H_{11})_3N$, $(C_6H_{13})_3N$, $C_6H_5CH_2NH_2$, $HOCH_2CH_2NH_2$, $(HOCH_2CH_2)_2NH$, $(HOCH_2CH_2)_3N$, $C_2H_5NH(CH_2CH_2OH)$, $C_2H_5N(CH_2CH_2OH)_2$, $(HOH_2C)_3CNH_2$ and

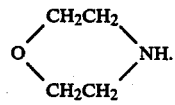

Further examples of other useful salts which can be prepared by the ion exchange technique are quaternary ammonium salts of phosphonoformic acid, i.e. salts in which 1-3 of the hydrogens in phosphonoformic acid (structural formula I) have been substituted with quaternary ammonium ions such as $(CH_3)_4N$, $(C_2H_5)_4N$, $(C_3H_7)_4N$, $(C_4H_9)_4N$, $(C_5H_{11})_4N$, $(C_6H_{13})_4N$ and $C_2H_5N(CH_2CH_2OH)_3$. Lipophilic salts of this type can also be prepared by mixing a salt of phosphonoformic acid with a quaternary ammonium salt in water and extracting out the resulting quaternary ammonium salt of phosphonoformic acid with an organic solvent such as dichloromethane, chloroform, ethyl acetate and methyl isobutyl ketone.

Pharmaceutical compositions

The following examples illustrate the preparation of pharmaceutical compositions of the invention. The phosphonoformic acid is preferably used in the form of its sodium salt.

EXAMPLE 3

Aerosol for inhalation

| | |
|---|---|
| Phosphonoformic acid (as its trisodium salt) | 1.00 g |
| Miglyol ® | 0.20 g |
| Frigen ® 11/12/113/114 ad | 100.0 g |

EXAMPLE 4

Tablets

Each tablet contains:

| | |
|---|---|
| Phosphonoformic acid (as its trisodium salt) | 20.0 mg |
| Maize starch | 25.0 mg |
| Lactose | 190.0 mg |
| Gelatin | 1.5 mg |
| Talc | 12.0 mg |
| Magnesium stearate | 1.5 mg |
| | 250.0 mg |

EXAMPLE 5

Suppositories

Each suppository contains:

| | |
|---|---|
| Phosphonoformic acid (as its trisodium salt) | 20.0 mg |
| Ascorbyl palmitate | 1.0 mg |
| Suppository base (Imhausen H or Witepsol ® H) ad | 2000.0 mg |

EXAMPLE 6

Syrup

| | |
|---|---|
| Phosphonoformic acid (as its trisodium salt) | 0.200 g |
| Liquid glucose | 30.0 g |
| Sucrose | 50.0 g |
| Ascorbic acid | 0.1 g |
| Sodium pyrosulfite | 0.01 g |
| Disodium edetate | 0.01 g |
| Orange essence | 0.025 g |
| Certified colour | 0.015 g |
| Purified water ad | 100.0 g |

EXAMPLE 7

Injection solution

| | |
|---|---|
| Phosphonoformic acid (as its trisodium salt) | 0.500 mg |
| Sodium pyrosulfite | 0.500 mg |
| Disodium edetate | 0.100 mg |
| Sodium chloride | 8.500 mg |
| Sterile water for injection ad | 1.00 ml |

EXAMPLE 8

Inhalation solution

| | |
|---|---|
| Phosphonoformic acid (as its trisodium salt) | 5.00 g |

-continued

| | |
|---|---|
| Sodium pyrosulfite | 0.10 g |
| Disodium edetate | 0.10 g |
| Sodium chloride | 0.85 g |
| Purified water ad | 100.0 ml |

EXAMPLE 9

Sublingual tablets

| | |
|---|---|
| Phosphonoformic acid (as its trisodium salt) | 5.0 mg |
| Lactose | 85.0 mg |
| Talc | 5.0 mg |
| Agar | 5.0 mg |
| | 100.0 mg |

EXAMPLE 10

Drops

| | |
|---|---|
| Phosphonoformic acid (as its trisodium salt) | 2.00 g |
| Ascorbic acid | 1.00 g |
| Sodium pyrosulfite | 0.10 g |
| Disodium edetate | 0.10 g |
| Liquid glucose | 50.00 g |
| Absolute alcohol | 10.00 g |
| Purified water ad | 100.0 ml |

EXAMPLE 11

Syrup

| | |
|---|---|
| Phosphonoformic acid (as its trisodium salt) | 0.200 g |
| Liquid glucose | 30.0 g |
| Sucrose | 50.0 g |
| Ascorbic acid | 0.1 g |
| Disodium edetate | 0.01 g |
| Orange essence with solubilizer | 0.25 g |
| Hydrochloric acid to pH 6.0–6.5 | |
| Purified water ad | 100.0 g |

EXAMPLE 12

Solution for injection

| | |
|---|---|
| Phosphonoformic acid (as its trisodium salt) | 0.500 mg |
| Disodium edetate | 0.100 mg |
| Sodium chloride | 8.500 mg |
| Hydrochloric acid to pH 6.5–7.0 | |
| Sterile water for injection ad | 1.00 ml |

EXAMPLE 13

Solution for inhalation

| | |
|---|---|
| Phosphonoformic acid (as its trisodium salt) | 5.00 g |
| Disodium edetate | 0.10 g |
| Sodium chloride | 0.85 g |
| Hydrochloric acid to pH 6.5–6.9 | |
| Purified water ad | 100.0 ml |

EXAMPLE 14

Drops

| | |
|---|---|
| Phosphonoformic acid (as its trisodium salt) | 2.00 g |

-continued

| | |
|---|---|
| Citric acid | 1.00 g |
| Disodium edetate | 0.10 g |
| Liquid glucose | 50.00 g |
| Ethanol 95% | 10.00 g |
| Sodium hydroxide and hydrochloric acid to pH 6.2–6.8 | |
| Purified water | ad 100.0 ml |

EXAMPLE 15

Solution for topical use

| | |
|---|---|
| Phosphonoformic acid (as its trisodium salt) | 2.00 g |
| Isopropanol | 38.0 g |
| Glycerol | 13.6 g |
| Hydrochloric acid to pH 5.0–7.0 | |
| Purified water | ad 100.0 g |

Preparations containing 0.2, 0.5 and 1.0 g of phosphonoformic acid trisodium salt have also been prepared.

EXAMPLE 16

Jelly

| | |
|---|---|
| Phosphonoformic acid (as its trisodium salt) | 4.0 g |
| Methocel ® | 4.0 g |
| Methyl paraoxybenzoate | 0.12 g |
| Propyl paraoxybenzoate | 0.05 g |
| Sodium hydroxide and hydrochloric acid to pH 6.7 | |
| Distilled water | ad 100.0 ml |

EXAMPLE 17

Ointment I

| | |
|---|---|
| Phosphonoformic acid (as its trisodium salt) | 2.5 g |
| Cetyltrimethylammonium bromide | 0.6 g |
| Stearyl alcohol | 2.25 g |
| Cetanol | 6.75 g |
| Liquid paraffine | 17.0 g |
| Glycerol | 12.0 g |
| Hydrochloric acid to pH 6.5 | |
| Distilled water | ad 100.0 g |

Preparations containing 0.2, 0.5, 1.0 and 2.0 g of phosphonoformic acid trisodium salt have also been prepared.

EXAMPLE 18

Ointment II

| | |
|---|---|
| Phosphonoformic acid (as its trisodium salt) | 2.5 g |
| Polyethylene glycol 1500 | 50 g |
| Polyethylene glycol 4000 | 15 g |
| Propylene glycol | ad 100 g |

EXAMPLE 19

Ointment III

| | |
|---|---|
| Phosphonoformic acid (as its trisodium salt) | 3.0 g |
| Sorbitan monoleate | 5.0 g |
| Petrolatum | ad 100 g |

EXAMPLE 20

Gastric juice-resistant tablets

Tablets according to Example 4 are coated with an enteric coating solution with the following composition:

| | |
|---|---|
| Cellulose acetate phtalate | 120.0 g |
| Propylene glycol | 30.0 g |
| Sorbitan monoleate | 10.0 g |
| Ethanol 95% | 450.0 ml |
| Acetone | q.s. ad 1000.0 ml |

The coating is carried out by a pouring procedure in a conventional coating pan or by spraying the tablets in a pan spray tablet coater.

EXAMPLE 21

Eye drops

| | |
|---|---|
| Active substance (as sodium salt) | 0.1 g |
| Disodium edetale | 0.10 g |
| Sodium chloride for isotonia q.s. | |
| Hydrochloric acid to pH 6.5–8.0 | |
| Methocel ® 65 HG 4000 | 0.65 |
| Sterile water | ad 100 ml |

EXAMPLE 22

Eye drops

| | |
|---|---|
| Active substance (as sodium salt) | 1.0 g |
| Disodium edetale | 0.10 g |
| Sodium chloride for isotonia q.s. | |
| Hydrochloric acid to pH 6.5–8.0 | |
| Methocel ® 65 HG 4000 | 0.65 |
| Sterile water | ad 100 ml |

EXAMPLE 23

Eye ointment

| | |
|---|---|
| Phosphonoformic acid (as its trisodium salt) | 5 g |
| Paraffin oil | 19 g |
| Petrolatum | 76 g |

EXAMPLE 24

Cream

| | |
|---|---|
| Trisodium phosphonoformate hexahydrate | 3.0 g |
| Arlaton ® | 4.0 g |
| Cetanol | 2.0 g |
| Stearic acid | 2.0 g |
| Paraffine oil | 2.0 g |
| Propylene glycol | 2.0 g |
| Glycerol | 1.5 g |
| Methyl-p-hydroxybensoate | 0.06 g |
| Propyl-p-hydroxybensoate | 0.03 g |
| Sodium hydroxide | 0.002 g |
| Hydrochloric acid 2 M to pH 8.0 (water phase) | |
| Distilled water | to 100 g |

EXAMPLE 25

Jelly

| | |
|---|---|
| Trisodiumphosphonoformate hexahydrate | 3.0 g |
| Methocel ® | 2.45 g |
| Glycerol | 10.0 g |
| Tween ® | 0.10 g |
| Methyl-p-hydroxybensoate | 0.06 g |
| Propyl-p-hydroxybensoate | 0.03 g |
| Sodium hydroxide | 0.002 g |
| Hydrochloric acid 2 M to pH 8.0 | |
| Distilled water | to 100 g |

What we claim is:

1. A method for the treatment of virus-induced diseases in animals including man, by inhibiting transformation of virus-infected cells, characterized by administering to an animal so infected an amount of phosphonoformic acid or a physiological salt thereof effective to inhibit the transformation of said virus-infected cells.

2. A method according to claim 1, wherein the infected animal is treated with the tri-sodium salt of phosphonoformic acid.

3. A method according to claim 2 wherein the trisodium salt of phosphonoformic acid is orally administered.

4. A method according to claim 1 wherein the phosphonoformic acid or physiologically effective salt thereof is orally administered.

5. A method for inhibiting the replication of a retrovirus in animals including man, comprising administering to an animal in need of such treatment phosphonoformic acid or a physiologically acceptable salt thereof in an amount sufficient for inhibiting said replication.

6. A method according to claim 5 wherein the phosphonoformic acid or physiologically effective salt thereof is orally administered.

7. A pharmaceutical composition effective for treating virus infections or diseases in animals and man suitable for oral administration to humans comprising as an active ingredient phosphonoformic acid or a physiologically acceptable salt thereof in an amount effective to inhibit replication of the virus or multiplication of a virus-transformed cell, together with a pharmaceutically acceptable carrier free of pharmaceutically unacceptable impurities and suitable for oral administration to humans.

8. A pharmaceutical composition according to claim 7 in which the active ingredient comprises about 0.1% to about 50% of the preparation.

* * * * *

UNITED STATES PATENT AND TRADEMARK OFFICE
CERTIFICATE OF CORRECTION

PATENT NO. : 4,771,041

DATED : Sept. 13, 1988

INVENTOR(S) : Eriksson et al.

Page 1 of 2

It is certified that error appears in the above-identified patent and that said Letters Patent is hereby corrected as shown below:

Col. 1, line 27, "use" should read --cause--; line 42, "replication of" should read --replication or--; line 64, "(reverse transcriptase)" should appear directly under "DNA polymerase" on the preceding line. Col. 2, line 10, "such a" should read --such as--; line 48, "selectivity" should read --selectively--; line 54, "varities" should read --varieties--. Col. 3, line 61, "mount" should read --amount--. Col. 4, delete lines 5 through 24. Col. 5, line 7, "inflicted" should read --afflicted--; line 10, delete "either"; line 52, "the" should read --oral--. Col. 6, line 3, "ascorbid" should read --ascorbic--; line 46, "invention" should read --infection--. Col. 7, line 16, "accid" should read --acid--; line 22, "Polymerases" should read --Polymerase--, and after "template" insert a comma; line 29, "generall" should read --generally--. Col. 8, line 45, "fraction" should read --fractions--. Col. 9, line 39, "reaction" should read --reduction--. Col. 14, line 33, "<1" should read --$\leq 1$--. Col. 15, line 48, "or" should read --on--. Col. 17, line 40, "$C_2H_5NH_2C_3H_7NH_2$" should read --$C_2H_5NH_2$, $C_3H_7NH_2$--]. Col. 18, line 14, "ad" should appear directly before "100.0 g"; line 38, "ad" should appear directly before "2000.0 mg"; line 51, "ad" should appear directly before "100.0 g"; line 61, "ad" should

UNITED STATES PATENT AND TRADEMARK OFFICE
CERTIFICATE OF CORRECTION

PATENT NO. : 4,771,041

DATED : Sept. 13, 1988

INVENTOR(S) : Eriksson et al.

It is certified that error appears in the above-identified patent and that said Letters Patent is hereby corrected as shown below:

appear directly before "1.00 ml". Col. 19, line 5, "ad" should appear directly before "100.0 ml"; line 28, "ad" should appear directly before "100.0 ml"; line 41, "ad" should appear directly before "100.0 g"; line 51, "ad" should appear directly before "1.00 ml"; line 61, "ad" should appear directly before "100.0 ml". Col. 21, line 24, "edetale" should read --edetate--; line 35, "edetale" should read --edetate--.

Signed and Sealed this

Sixth Day of June, 1989

Attest:

DONALD J. QUIGG

Attesting Officer

Commissioner of Patents and Trademarks